US007993903B2

(12) United States Patent
Hayakawa et al.

(10) Patent No.: US 7,993,903 B2
(45) Date of Patent: Aug. 9, 2011

(54) CHOLESTEROL ABSORPTION INHIBITOR

(75) Inventors: Hiroko Hayakawa, Minato-ku (JP); Tohru Iino, Minato-ku (JP); Fumiyasu Ishikawa, Minato-ku (JP)

(73) Assignee: Kabushiki Kaisha Yakult Honsha, Minato-ku (JP)

( * ) Notice: Subject to any disclaimer, the term of this patent is extended or adjusted under 35 U.S.C. 154(b) by 573 days.

(21) Appl. No.: 12/066,212

(22) PCT Filed: Sep. 7, 2006

(86) PCT No.: PCT/JP2006/317748
§ 371 (c)(1),
(2), (4) Date: Mar. 7, 2008

(87) PCT Pub. No.: WO2007/029773
PCT Pub. Date: Mar. 15, 2007

(65) Prior Publication Data
US 2009/0170185 A1    Jul. 2, 2009

(30) Foreign Application Priority Data
Sep. 8, 2005  (JP) ................................ 2005-260401

(51) Int. Cl.
C12N 1/12       (2006.01)
A23C 9/12       (2006.01)
A23C 17/00      (2006.01)
A01N 63/00      (2006.01)
(52) U.S. Cl. ......... 435/252.1; 426/61; 426/43; 424/93.4
(58) Field of Classification Search ............... 435/252.1; 426/61, 43; 424/93.4
See application file for complete search history.

(56) References Cited

U.S. PATENT DOCUMENTS
2004/0208859 A1   10/2004   Yokota et al.

FOREIGN PATENT DOCUMENTS

| EP | 0 181 170 | 5/1986 |
| EP | 1 421 945 A1 | 5/2004 |
| JP | 61 109729 | 5/1986 |
| JP | 61-271223 | 12/1986 |
| JP | 62 258323 | 11/1987 |
| JP | 62-258323 | 11/1987 |
| JP | 8-256762 | 10/1996 |
| JP | 2003 238423 | 8/2003 |
| WO | 2003 013559 | 2/2003 |

OTHER PUBLICATIONS

Xiao, Jin-zhong, "Effect of Fermented Milks on Blood Lipids", Milk Science, vol. 52, No. 3, pp. 161 to 165, 2003. (with Partial English Translation).
Hosono, Akiyoshi, "Function of Lactic Acid Bacteria for the Health", Bulletin of Japan Dairy Technical Association, vol. 50, pp. 92 to 116, 2000. (with Partial English Translation).
Abd El-Gawad, Ibrahim A., et al., "The Hypocholesterolaemic Effect of Milk Yoghurt and Soy-Yoghurt Containing *Bifidobacteria* in Rats Fed on a Cholesterol-Enriched Diet", International Dairy Journal, vol. 15, No. 1, pp. 37 to 44, 2005.
Gonzalez Vara, Antonio, et al., "Stability of Recombinant Plasmids on the Continuous Culture of *Bifidobacterium animalis* ATCC 27536", Biotechnology and Bioengineering, vol. 84, No. 2, pp. 145 to 150, 2003.
Masco, Liesbeth et al., "Polyphasic Taxonomic Analysis of *Bifidobacterium animalis* and *Bifidobacterium lactis* Reveals Relatedness at the Subspecies Level: Reclassification of *Bifidobacterium animalis* as *Bifidobacterium animalis* Subsp. *Animalis* Sub Sp. Nov. and *Bifidobacterium lactis* as *Bifidobacterium animalis* Subsp. *Lactis* Subsp. Nov.", International Journal of Systematic and Evolutionary Microbiology, vol. 54, No. 4, pp. 1137 to 1143, 2004.
Matsumoto, Mitsuharu, "Novel Enteric Environment Improving Effects of Yogurt", vol. 107, No. 3, pp. 304 to 309, 2005. (with Partial English Translation).
Daniel Vincent, et al., "Characterization of *Bifidobacteria* by random DNA amplification", International Journal of Food Microbiology, vol. 43, XP-002536589, Sep. 8, 1998, pp. 185-193.
K. Tahri, et al., "Effects of three strains of *Bifidobacteria* on cholesterol", Letters in Applied Microbiology, vol. 21, XP-002536590, 1995, pp. 149-151.
J. Z. Xiao, et al., "Effects of Milk Products Fermented by *Bifidobacterium longum* on Blood Lipids in Rats and Healthy Adult Male Volunteers", Journal of Dairy Science, vol. 86, No. 7, XP-002536591, Jul. 2003, pp. 2452-2461.
Hoo-Kil Jung, et al., "Comparative Evaluation of Probiotic Activities of *Bifidobacterium longum* MK-G7 with Commercial *Bifidobacteria* Strains", Journal of Microbiology and Biotechnology, vol. 10, No. 2, XP-009040427, Apr. 7, 2000, pp. 147-153.
Angeline Gopal, et al., "Bile tolerance, taurocholate deconjugation and cholesterol removal by *Lactobacillus acidophilus* and *Bifidobacterium* spp." Milchwissenschaft, vol. 51, No. 11, XP-009119761, Jan. 1, 1996, pp. 619-623.
P. Leperq, et al., "*Bifidobacterium animalis* Strain DN-173 010 Hydrolyses Bile Salts in the Gastrointestinal Tract of Pigs", Scandanavian Journal of Gastroenterology, vol. 39, No. 2 , XP-009119680, Dec. 1, 2004, pp. 1266-1271.
H. Tanaka, et al., "Screening of Lactic Acid Bacteria for Bile Salt Hydrolase Activity", Journal of Dairy Science, vol. 82, No. 12, XP-002536592, Dec. 1999, pp. 2530-2535.
P. J. Simpson, et al., "Genomic Diversity and Relatedness of *Bifidobacteria* Isolated from a Porcine Cecum", Journal of Bacteriology, vol. 185, No. 8, Apr. 2003, pp. 2571-2581.
Seiichiro A., et al, "Effect of lactic acid bacteria and enteric bacteria on cholesterol metabolism in rat", The 6th Japan Bifidus Foundation, Annual Meeting proceedings, May 24, 1986, p. 11 (with English translation).

Primary Examiner — Ganapathirama Raghu
(74) Attorney, Agent, or Firm — Oblon, Spivak, McClelland, Maier & Neustadt, L.L.P.

(57) ABSTRACT

To provide a bacterium belonging to the genus *Bifidobacterium* which is excellent in a survival ability in the gastrointestinal tract, has an effect of inhibiting the cholesterol absorption in the intestinal tract, and is excellent in lipid metabolism ameliorating effects including decreasing the blood cholesterol level and the like, and shows a high survival rate after storage, and a cholesterol absorption inhibitor using the same. The invention provides a cholesterol absorption inhibitor containing, as an active ingredient, at least one microorganism selected from *Bifidobacterium animalis* subsp. *animalis* YIT 10394, *Bifidobacterium animalis* subsp. *lactis* JCM 1253, *Bifidobacterium animalis* subsp. *lactis* JCM 7117, and *Bifidobacterium pseudolongum* subsp. *globosum*.

8 Claims, No Drawings

US 7,993,903 B2

CHOLESTEROL ABSORPTION INHIBITOR

TECHNICAL FIELD

The present invention relates to bacteria belonging to the genus *Bifidobacterium* which have an excellent effect of inhibiting the cholesterol absorption, and a cholesterol absorption inhibitor containing these bacteria belonging to the genus *Bifidobacterium* as an active ingredient.

BACKGROUND ART

Cholesterols exist in many cells and primarily play physiological roles of maintaining cellular functions as components of lipoproteins or biological membranes, serving as raw material for bile acid and various hormones, and the like. However, it is known that increased serum cholesterol levels resulting from excessive intake of foods with a high content of cholesterols lead to arteriosclerosis. In the modern dietary life with many opportunities of taking cholesterols, it is required to suppress the concentration of cholesterols in the body.

Furthermore, it has been reported that bacterial cells of *Bifidobacterium bifidum*, *Bifidobacterium adolescentis*, *Bifidobacterium breve*, *Bifidobacterium infantis*, and *Bifidobacterium longum* have blood lipid ameliorating effects (Patent Document 1). In particular, *Bifidobacterium longum* has been well studied, and reports have shown that *Bifidobacterium longum* SBT 2933R (FERM P-8743) has excellent effects (Non-patent Document 1), and use of cells of this bacterium or a culture thereof as a serum cholesterol elevation inhibitor has been proposed (Patent Document 2). In general, however, bacteria belonging to the genus *Bifidobacterium* are weak against oxygen as well as gastric acid and bile acid in the body. Therefore, there is a problem that, when cells of this bacterium or a culture thereof is orally taken, the cells have a poor survival ability in the gastrointestinal tract and show inadequate effects in many cases. Accordingly, bacteria belonging to the genus *Bifidobacterium* which have an excellent survival ability and a serum cholesterol elevation inhibiting effect have been desired.

However, it is only known about such bacteria belonging to the genus *Bifidobacterium* having an excellent survival ability that *Bifidobacterium longum* SBT 10254 (FERM P-14820) (Patent Document 3) and *Bifidobacterium longum* (FERM BP-7787) (Patent Document 4) have an excellent survival ability and show a serum cholesterol elevation inhibiting effect, that *Bifidobacterium longum* BB536, *Bifidobacterium breve* ATCC 15700, and *Bifidobacterium animalis* ATCC 25527 (Non-patent Document 2) show a cholesterol sedimentation effect, and the like. In the current situation, there are few options of microorganisms which have an excellent survival ability and a cholesterol inhibiting effect.

Furthermore, since it is often inevitable to store drugs or foods using these microorganisms for a long period, high storage stability is required. However, known microorganisms have a poor survival ability after long-term storage, and many of them have a poor survival ability, particularly under a non-anaerobic condition.

[Patent Document 1] JP-A-61-271223
[Patent Document 2] JP-B-6-96537
[Patent Document 3] JP-B-3384907
[Patent Document 4] JP-A-2003-238423
[Non-patent Document 1] The 6th Japan Bifidus Foundation, Annual Meeting Proceedings, p. 18, 1987
[Non-patent Document 2] Letters in Applied Microbiology, Vol. 21, 149-151, 1995

DISCLOSURE OF THE INVENTION

Problems to be Solved by the Invention

Accordingly, an object of the present invention is to provide a bacterium belonging to the genus *Bifidobacterium* which shows an excellent survival ability in the gastrointestinal tract, has effects of inhibiting the cholesterol absorption in the intestinal tract, is excellent in lipid metabolism ameliorating effects including decreasing the blood cholesterol level, and shows a high survival rate after storage, and a cholesterol absorption inhibitor using the same.

Means for Solving the Problems

The inventors of the present invention conducted various researches to achieve the foregoing object. As a result, they surprisingly found that *Bifidobacterium animalis* subsp. *animalis* YIT 10394, *Bifidobacterium animalis* subsp. *lactis* JCM 1253, *Bifidobacterium animalis* subsp. *lactis* JCM 7117, and *Bifidobacterium pseudolongum* subsp. *globosum* are excellent in cholesterol eliminating effects, show potent acid tolerance and bile acid tolerance, further have an excellent effect of inhibiting cholesterol absorption in the intestines, and show a high survival ability after storage, in particular, a high survival rate after storage even under a non-anaerobic condition. Thus, the present invention was accomplished. Of the microorganisms used in the present invention, *Bifidobacterium animalis* subsp. *animalis* YIT 10394, *Bifidobacterium pseudolongum* subsp. *globosum* YIT 10392, and *Bifidobacterium pseudolongum* subsp. *globosum* YIT 10393 are microorganisms newly discovered by the inventors of the present invention.

Specifically, the present invention provides a cholesterol absorption inhibitor comprising, as an active ingredient, at least one microorganism selected from *Bifidobacterium animalis* subsp. *animalis* YIT 10394, *Bifidobacterium animalis* subsp. *lactis* JCM 1253, *Bifidobacterium animalis* subsp. *lactis* JCM 7117, and *Bifidobacterium pseudolongum* subsp. *globosum*.

Furthermore, the present invention provides a cholesterol absorption inhibitor comprising, as an active ingredient, at least one microorganism selected from *Bifidobacterium animalis* subsp. *lactis* JCM 1253 and *Bifidobacterium animalis* subsp. *lactis* JCM 7117.

Furthermore, the present invention provides a cholesterol absorption inhibitor comprising, as an active ingredient, at least one microorganism selected from *Bifidobacterium animalis* subsp. *animalis* YIT 10394, *Bifidobacterium pseudolongum* subsp. *globosum* YIT 10392, and *Bifidobacterium pseudolongum* subsp. *globosum* YIT 10393.

Furthermore, the present invention provides novel microorganisms, *Bifidobacterium animalis* subsp. *animalis* YIT 10394 (FERM ABP-10662), *Bifidobacterium pseudolongum* subsp. *globosum* YIT 10392 (FERM ABP-10660), and *Bifidobacterium pseudolongum* subsp. *globosum* YIT 10393 (FERM ABP-10661).

Since *Bifidobacterium animalis* subsp. *animalis* YIT 10394, *Bifidobacterium animalis* subsp. *lactis* JCM 1253, *Bifidobacterium animalis* subsp. *lactis* JCM 7117, and *Bifidobacterium pseudolongum* subsp. *globosum* of the present invention not only have an excellent cholesterol eliminating effect but also are excellent in acid tolerance and bile-acid tolerance, they also show an excellent effect of inhibiting the cholesterol absorption in the intestines and can be utilized for the purpose of ameliorating the lipid metabolism, for example, decreasing the blood cholesterol level. Furthermore, since these microorganisms have a high survival rate after storage, in particular, a high survival rate even after storage under a non-anaerobic condition, the cholesterol absorption inhibitor of the present invention can be stored for a long period as well as under a non-anaerobic condition.

BEST MODE FOR CARRYING OUT THE INVENTION

Examples of *Bifidobacterium pseudolongum* subsp. *globosum* used in the present invention include *Bifidobacterium pseudolongum* subsp. *globosum* YIT 10392 and *Bifidobacterium pseudolongum* subsp. *globosum* YIT 10393.

These *Bifidobacterium pseudolongum* subsp. *globosum* YIT 10392, *Bifidobacterium pseudolongum* subsp. *globosum* YIT 10393, and *Bifidobacterium animalis* subsp. *animalis* YIT 10394, one of the microorganisms used in the present invention, are novel bacterial strains isolated by the inventors of the present invention as bacterial strains having properties such as showing a cholesterol eliminating activity of 70% or higher, a survival rate of 20% or higher in an artificial gastric juice, and a proliferation rate of 100 or higher, as a Klett value (bacterial cell turbidity), in a bile-acid-containing medium. These bacterial strains have the following microbiological properties. Specifically, all these bacterial strains are Gram-positive polymorphic bacilli which are nonspore-forming, nonmotile, and obligate anaerobic, can grow at 37° C., and show properties of *Bifidobacterium pseudolongum* subsp. *globosum*, *Bifidobacterium pseudolongum* subsp. *globosum*, *Bifidobacterium animalis* subsp. *animalis*, respectively, in this order, apart from the cholesterol eliminating activity, the survival rate in an artificial gastric juice, and the proliferation rate in a bile-acid-containing medium shown above.

The species of these novel bacterial strains were identified based on the findings in the bacterial species identification using 16S rDNA nucleotide sequence that the 16S rDNA nucleotide sequence of YIT 10392 shows a homology of 99.6% with that of *Bifidobacterium pseudolongum* subsp. *globosum* (Accession No. D86194), the 16S rDNA nucleotide sequence of YIT 10393 shows a homology of 99.6% with that of *Bifidobacterium pseudolongum* subsp. *globosum* (Accession No. D86194), and the 16S rDNA nucleotide sequence of YIT 10394 shows a homology of 99.7% with that of *Bifidobacterium animalis* subsp. *animalis* (Accession No. D86185). Here, the bacterial species identification using 16S rDNA nucleotide sequence was performed by amplifying the full-length of a 16S rDNA sequence by PCR using, as a template, DNA extracted from bacterial cells obtained by centrifugal washing of bacterial solution cultured anaerobically (carbon dioxide substitution) using a 0.5%-glucose-added GAM medium at 37° C. for 24 hours, determining the nucleotide sequence of the amplification product by the dye terminator method, and searching the obtained nucleotide sequence in a database. Furthermore, these bacterial strains were determined to be novel based on the findings that their 16S rDNA nucleotide sequences were different from those of the type strains, and the results of chromosome DNA polymorphism analysis by the Random Amplified Polymorphic DNA (RAPD) method were different.

*Bifidobacterium animalis* subsp. *animalis* YIT 10394, *Bifidobacterium pseudolongum* subsp. *globosum* YIT 10392, and *Bifidobacterium pseudolongum* subsp. *globosum* YIT 10393 were transferred as Accession Nos. FERM ABP-10662, FERM ABP-10660 and FERM ABP-10661, respectively, to International Patent Organism Depositary, National Institute of Advanced Industrial Science and Technology on Aug. 14, 2006. These microorganisms had been deposited at the same organization on Aug. 18, 2005 before the transfer. The postal address of this depositary is zip code 305-8566, Tsukuba Central 6, 1-1-1 Higashi, Tsukuba, Ibaraki, Japan.

Furthermore, both *Bifidobacterium animalis* subsp. *lactis* JCM 1253 and *Bifidobacterium animalis* subsp. *lactis* JCM 7117 used in the present invention can be purchased from Japan Collection of Microorganisms (JCM) and American Type Culture Collection (ATCC), and ATCC numbers thereof are ATCC 27536 and ATCC 27674, respectively.

Of these, a microorganism whose survival rate is 50% or higher when a fermented milk food or drink produced using the microorganism is stored at 10° C. for 21 days under a non-anaerobic (aerobic) condition is preferred as the microorganism used in the present invention.

Furthermore, as the microorganisms of the present invention, bacteria belonging to the genus *Bifidobacterium* with a cholesterol eliminating activity of 70% or higher are preferred, and bacteria belonging to the genus *Bifidobacterium* with a cholesterol eliminating activity of 70% or higher, a survival rate of 20% or higher in an artificial gastric juice, and a proliferation rate of 100 or higher, as the Klett value (bacterial cell turbidity), in a bile-acid-containing medium are more preferred. Common bacteria belonging to the genus *Bifidobacterium*, have a survival rate of about 0 to several percents in an artificial gastric juice and a proliferation rate of about 0 to several tens, as the Klett value (bacterial cell turbidity), in a bile-acid-containing medium. Many cells of bacteria having high acid tolerance and bile acid tolerance which are selected based on the above-mentioned value can reach the intestines in a viable state.

Here, the cholesterol eliminating activity can be calculated by, for example, measuring the cholesterol level in the supernatant according to a usual method after microorganism cells are allowed to stand together with artificial lipid micelles, comparing with the cholesterol level in a supernatant not containing bacterial cells, and inserting the values into the following equation.

Cholesterol eliminating activity(%)=100−(cholesterol level in supernatant containing bacterial cells)/(cholesterol level in supernatant not containing bacterial cells)×100

Furthermore, the survival rate in an artificial gastric juice can be defined as, for example, the survival rate after storage in an artificial gastric juice of pH 3.0 at 37° C. for 1 hour. When this value is high, it means that the survival rate in the gastrointestinal tract is high.

Furthermore, the proliferation rate in a bile-acid-containing medium can be defined as, for example, turbidity upon culture in a medium containing 0.2% bile acid at 37° C. for 24 hours expressed with a Klett value (Klett-Summerson Colorimeter, No. 66 Filter). When this value is high, the survival rate and the proliferation rate in the gastrointestinal tract are high.

Since genus, species, and strain names of a microorganism vary depending on the person who designated the microorganism and are also uncertain due to reclassifications of bacteria or the like, microorganisms which are substantially identical are included in the microorganisms of the present invention even though they have different genus, species, or bacterial strain names. Specifically, for example, although *Bifidobacterium animalis* and *Bifidobacterium lactis* have been regarded as separate species, Masco et al. have collectively classified these microorganisms as *Bifidobacterium animalis*, which is further divided into two subspecies, *Bifi-* dobacterium animalis subsp. animalis and Bifidobacterium animalis subsp. lactis, as subclasses (Int. J. Syst. Envol. Microbiol. 54, 1137-1143, 2004). This classification remains to date. Therefore, bacteria used to be referred to as Bifidobacterium animalis and Bifidobacterium lactis also fall within the scope of Bifidobacterium animalis subsp. animalis and Bifidobacterium animalis subsp. lactis, respectively, of the present invention.

Furthermore, Bifidobacterium animalis subsp. lactis ATCC 27536 is identical to Bifidobacterium animalis subsp. lactis JCM 1253, and Bifidobacterium animalis subsp. lactis ATCC 27674 is identical to Bifidobacterium animalis subsp. lactis JCM 7117. All of these are included in the microorganisms of the present invention. All these bacterial strains are classified as Bifidobacterium animalis subsp. animalis in JCM and ATCC. However, since the 16S rDNA nucleotide sequences of these two bacterial strains 100% matched those of Bifidobacterium animalis subsp. lactis (Accession No. X89513), these strains are classified as Bifidobacterium animalis subsp. lactis in the present invention.

Since the microorganisms of the present invention have a cholesterol eliminating activity and decrease the cholesterol level, in particular, the blood cholesterol level as shown in the examples described later, agents containing these microorganisms in an effective amount are useful as cholesterol absorption inhibitors, in particular, as inhibitors of cholesterol absorption from the intestinal tract. It is expected that the cholesterol absorption inhibitor of the present invention can be used for decreasing the levels of blood cholesterols, triglyceride, and VLDL and LDL cholesterols, and the arteriosclerosis index, ameliorating the lipid metabolism including elevating HDL cholesterol, ameliorating hyperlipemia, which often develops due to postmenopausal lack of female sex hormones, and decreasing a risk of developing arteriosclerosis.

Furthermore, since the microorganisms of the present invention show acid tolerance and bile-acid tolerance as shown in the examples described later, agents containing these microorganisms in an effective amount can be used as cholesterol absorption inhibitors for oral administration.

Furthermore, since the microorganisms of the present invention have a high survival ability even after storage in a fermented milk food or drink under an aerobic (non-anaerobic) condition as shown in the examples described later, agents containing these microorganisms in an effective amount can be used as cholesterol absorption inhibitors stored under an aerobic (non-anaerobic) condition. The storage temperature can be set at, for example, −80 to 10° C.

It is sufficient that the cholesterol absorption inhibitor of the present invention comprises, as an active ingredient, at least one microorganism selected from Bifidobacterium animalis subsp. animalis YIT 10394, Bifidobacterium animalis subsp. lactis JCM 1253, Bifidobacterium animalis subsp. lactis JCM 7117, and Bifidobacterium pseudolongum subsp. globosum. Examples of a combination of microorganisms used here include at least one combination selected from Bifidobacterium animalis subsp. lactis JCM 1253 and Bifidobacterium animalis subsp. lactis JCM 7117 and at least one combination selected from Bifidobacterium animalis subsp. animalis YIT 10394, Bifidobacterium pseudolongum subsp. globosum YIT 10392, and Bifidobacterium pseudolongum subsp. globosum YIT 10393.

Furthermore, the cholesterol absorption inhibitor of the present invention uses Bifidobacterium animalis subsp. animalis YIT 10394, Bifidobacterium animalis subsp. lactis JCM 1253, Bifidobacterium animalis subsp. lactis JCM 7117, and Bifidobacterium pseudolongum subsp. globosum solely or in combination or can use these microorganisms in combination with other microorganisms. Examples of such microorganisms include bacteria belonging to the genus Bifidobacterium such as Bifidobacterium animalis subsp. animalis, Bifidobacterium animalis subsp. lactis, Bifidobacterium pseudolongum subsp. globosum, Bifidobacterium adolescentis, Bifidobacterium angulatum, Bifidobacterium asteroides, Bifidobacterium bifidum, Bifidobacterium breve, Bifidobacterium catenulatum, Bifidobacterium dentium, Bifidobacterium gallicum, Bifidobacterium infantis, Bifidobacterium longum, Bifidobacterium pseudocatenulatum, Bifidobacterium pseudolongum subsp. pseudolongum, Bifidobacterium suis, and Bifidobacterium thermophilum; bacteria belonging to the Lactobacillus such as Lactobacillus acidophilus, Lactobacillus gasseri, Lactobacillus plantarum, Lactobacillus casei, Lactobacillus johnsonii, Lactobacillus crispatus, Lactobacillus rhamnosus, Lactobacillus kefiri, Lactobacillus delbrueckii subsp. delbrueckii, Lactobacillus delbrueckii subsp. bulgaricus, Lactobacillus helveticus, Lactobacillus salivarius, Lactobacillus reuteri, Lactobacillus mali, Lactobacillus amylovorus, Lactobacillus alimentarius, Lactobacillus buchneri, Lactobacillus brevis, Lactobacillus gallinarum, Lactobacillus fermentum, Lactobacillus maltaromicus, Lactobacillus paracasei, and Lactobacillus pentosus; bacteria belonging to the genus Streptococcus such as Streptococcus thermophilus; bacteria belonging to the genus Lactococcus such as Lactococcus lactis subsp. cremoris and Lactococcus lactis subsp. lactis; bacteria belonging to the genus Leuconostoc such as Leuconostoc mesenteroides subsp. cremoris; bacteria belonging to the genus Pediococcus such as Pediococcus cerevisiae; bacteria belonging to the genus Enterococcus such as Enterococcus faecalis; bacteria belonging to the genus Acetobacter such as Acetobacter aceti; bacteria belonging to the genus Gluconobacter such as Gluconobacter oxydans; bacteria belonging to the genus Bacillus such as Bacillus subtilis; yeasts belonging to the genus Saccharomyces such as Saccharomyces cerevisiae; yeasts belonging to the genus Torulaspora such as Torulaspora debrueckii; yeasts belonging to the genus Candida such as Candida kefiri; yeasts belonging to the genus Kluyveromyces such as Kluyveromyces marxianus; yeasts belonging to the genus Debaryomyces such as Debaryomyces hansenii; yeasts belonging to the genus Pichia such as Pichia anomala; yeasts belonging to the genus Zygosaccharomyces such as Zygosaccharomyces rouxii; fungi belonging to the genera Aspergillus, Mucor, Monascus, Penicillium, Rhizomucor, and Rhizopus such as Aspergillus oryzae, Mucor japonicus, Monascus purpureus, Penicillium camemberti, Rhizomucor pusillus, and Rhizopus arrhizus.

Further, the microorganisms contained in the cholesterol absorption inhibitor of the present invention may be lyophilized or utilized as a culture containing these microorganisms. In any form, it is preferable that microorganisms are in the state of viable cells.

The cholesterol absorption inhibitor of the present invention can be administered in the form of a commonly used drug formulation by mixing the above-mentioned microorganisms with solid or liquid pharmaceutical nontoxic carriers. Examples of such a formulation include solid formulations such as tablet, granule, powder, and capsule, liquid formulations such as solutions, suspensions, and emulsions, lyophilized formulations. These formulations can be prepared by usual measures for manufacturing formulations. Examples of the pharmaceutical nontoxic carriers include glucose, lactose, sucrose, starch, mannitol, dextrin, fatty acid glyceride, polyethylene glycol, hydroxyethyl starch, ethylene glycol, polyoxyethylene sorbitan fatty acid esters, amino acids, gelatin, albumin, water, physiological saline. Furthermore, commonly used additives such as stabilizers, wetting agents, emulsifiers, binders, and isotonizing agents can be suitably added as required.

Furthermore, the cholesterol absorption inhibitor of the present invention can be taken as the above-mentioned microorganisms as they are, by adding directly to a food, or in the form of a food or drink. Preferred examples of the food or drink include fermented milk, fermented soy milk, fermented fruit juice, fermented plant juice, fermented rice juice, fermented wort, and fermented foods and drinks using materials derived from animals or plants (pickles, fermented soybean paste, soy sauce, fermented tea, fermented sausages, fermented mayonnaise, cheese, salted fish guts, etc.) which comprise the microorganisms of the present invention in the state of viable cells. The food or drink can be manufactured by a usual method. For example, when fermented milk is manufactured, first, a fermented milk base is obtained by inoculating and culturing at least one of *Bifidobacterium animalis* subsp. *animalis* YIT 10394, *Bifidobacterium animalis* subsp. *lactis* JCM 1253, *Bifidobacterium animalis* subsp. *lactis* JCM 7117, and *Bifidobacterium pseudolongum* subsp. *globosum* solely or together with other microorganisms in a sterilized milk medium, and homogenizing the medium. Then, a separately prepared syrup solution is added and mixed, and the mixture is homogenized with a homogenizer or the like, and a flavor is further added to complete a final product. The fermented milk of the present invention thus obtained can be prepared as a product in any form such as of a plain type, soft type, or fruit flavor type, in a solid, liquid, or frozen state, or the like. Animal feeds are also included in the food or drink. The microorganism of the present invention in fermented milk can be contained, for example, at a concentration of $10^3$ to $10^{13}$ cfu/mL.

In this case, the cholesterol absorption inhibitor of the present invention can be mixed with food materials commonly used in foods and drinks such as, for example, saccharides, proteins, peptides, lipids, vitamins, minerals, plant components such as vegetables, grains, and fruit, animal components such as blood, milk, liver, bones, and muscles, microorganism components such as bacteria, fungi, yeasts, and mushrooms, culture components thereof, gelatinizing agents, fixation agents, thickening agents, flavors, coloring agents, *Bifidobacterium* bacteria growth promoting agents, lactic acid bacteria growth promoting agents. Specific examples thereof include various sweeteners such as glucose, sucrose, fructose, maltose, isoglucose, xylose, palatinose, honey, maple syrup, and amazake, various sugar alcohols such as sorbitol, xylitol, erythritol, lactitol, palatinit, reduced starch syrup, and reduced maltose syrup, various highly sweet sweeteners such as sucralose and aspartame, various natural sweeteners such as licorice, stevia, and glycyrrhizinic acid glycoside, various emulsifiers such as sucrose fatty acid esters, glycerine sugar fatty acid esters, and lecithin, and various thickening (stabilizing) agents such as agar, gelatin, carrageenan, guar gum, gum arabic, xanthan gum, pectin, and locust bean gum.

In addition, examples of the food materials also include various carbohydrates such as tagatose, lactose, trehalose, trehallose, agarooligosaccharide, nigerooligosaccharide, galactooligosaccharide, fructooligosaccharide, xylooligosaccharide, raffinose, stachyose, lactulose, maltotriose, isomaltooligosaccharide, cyclodextrin, glucosamine, and N-acetylglucosamine, various dietary fibers such as algic acid, sodium alginate, fucoidan, sargassan, furceran, funoran, porphyran, aminaran, Pullulan, taragum, konjak mannan, inulin, chitin, chitosan, polydextrose, hyaluronic acid, chondroitin sulfate, β-glucan, mannan, galactan, fructan, xylan, arabinan, arabinogalactan, glucomannan, galactomannan, beet fiber, oat fiber, wheat fiber, soybean fiber, rice fiber, barley fiber, xanthan gum, corn fiber, apple fiber, citrus fiber, Psyllium fiber, pine fiber, prune fiber, pea fiber, banana fiber, acetic acid bacteria cellulose, lactic acid bacteria cell wall, *Bifidobacterium* bacteria cell wall, yeast cell wall, natto fructan, collagen, and natto polyglutamic acid or various hydrolysates of these dietary fibers, and various materials containing indigestible dietary fibers such as wheat bran, barley bran, rice bran, *Avena fatua* bran, oat bran, rye bran, Psyllium, rice bran powder, brown rice, chicory, bean curd refuse, apple pulp, resistant starch, barley malt, maize seed hull, lactic acid bacteria cells, *Bifidobacterium* bacteria cells, beer yeast cells, wine yeast cells, wine lees, sake lees, soy sauce lees, beer lees, malted rice, malted wheat, malted beans, Monascus pilosus, *Aspergillus oryzae*, viscous substance of fermented soybean, grape seed extract, royal jelly, propolis, chlorella, spirulina, euglena, undaria, sea tangle, sea grape, eisenia, *Eisenia bicyclis, Porphyra tenera*, green layer, hizikia, ulvaceae, and *Nemacystus decipiens*.

Further, examples of the food materials include various minerals such as calcium, magnesium, zinc, iron, manganese, iodine, selenium, copper, cobalt, and dolomite and various salts of these minerals, various acids such as citric acid, malic acid, tartaric acid, pyruvic acid, gluconic acid, succinic acid, fumaric acid, ascorbic acid, lactic acid, acetic acid, propionic acid, butyric acid, phosphoric acid, and amino acids such as creatine, methionine, cysteine, and glutamic acid and various salts of these acids, various components such as glutathione, phytin, phytic acid, lignin, poly-γ-glutamic acid and degradation products thereof, saponin, ferulic acid, γ-aminobutyric acid, γ-oryzanol, chalcone, flavanone, flavone, flavonol, isoflavone, anthocyan, catechin, proanthocyanidin, tea leaf polyphenol, curcumide, capsaicinoid, sesaminol, sesame lignan, theaflavin, β-diketones, carotenoids, allyl sulfur compounds, isothiocyanates, terpenes, chlorophylls, sphingolipids, ganglioside, n-3 polyunsaturated fatty acids, n-6 polyunsaturated fatty acids, conjugated linoleic acids, phospholipids, and plant sterols, various proteins such as soybean proteins such as glycinin and conglycinin, egg proteins such as ovoalbumin and ovomucoid, lactoproteins and whey proteins such as casein, lactalbumin, and lactoferrin, rice proteins such as casein phosphopeptide and oryzenin, wheat proteins such as glutenin and gliadin, and fish proteins and enzyme-degraded peptides and acid-degraded peptides thereof, various vitamins such as vitamin A, vitamin B family, vitamin C, vitamin D family, vitamin E, vitamin K family, β-carotene, retinoic acid, and folic acid, various extracts of black cohosh, pumpkin seed, pomegranate seed, St. John's wort, passionflower, valerian, *Pueraria mirifica*, rosemary, peppermint, parsley, marigold, lemon balm, mugwort, safflower, Japanese radish seed, coffee tree, araliad, gourd fruit, citrus peels, ginkgo leaf, jujube, lycii fructus, licorice, Ganoderma lucidum, ginseng, guarana, and the like, various plant extracts of green tea, black tea, oolong tea, gymnema tea, guava tea, and the like, and various spices such as pepper, Zanthoxylum, cinnamon, turmeric, sage, thyme, basil, red pepper, and nutmeg.

Further, examples of the food materials include various grain components such as rice, brown rice, barley, wheat, oat, rye, adlay, amaranth, *Setaria italica, Panicum miliaceum*, buck wheat, Sorghum bicolor, and maize and various sprout components of seeds of these grains, various vegetable components such as adzuki bean, white adzuki bean, kintoki bean, kidney bean, *Pisum sativum*, flower bean, chana bean, black soybean, blue soybean, mung bean, broad bean, daifuku bean, *Angelica keiskei*, kale, curcuma, potato, sweet potato, purple sweet potato, Japanese yam, pumpkin, eggplant, tomato, bitter melon, capsicum, sesame, cabbage, broccoli, cauliflower, lettuce, green soybean, ginger, burdock, celery, Japanese radish, Japanese horseradish, avocado, carrot, spinach, onion, garlic, lily, scallion, *Perilla frutescens crispa*, spring onion, Allium odorum, parsnip, *Pteridium aquilinum*, bamboo shoot, Shiitake mushroom, and mushroom, fruit components such as lemon, apple, grape, strawberry, orange, persimmon, guava, banana, blueberry, blackberry, cranberry, raspberry, cowberry, bayberry, feijoa, tree tomato, acerola, lime, *Citrus depressa*, melon, peach, mango, Chinese lemon, papaya, pineapple, pear, plum, grapefruit, Chinese quince, apricot, mandarin, pomegranate, watermelon, prune, and kiwi fruit, various nut components such as peanut, almond, coconut, cashew nut, macadamia nut, cacao, chestnut, ginkgo nut, and walnut, various dairy products such as cow's milk, skimmed milk, whey, cream, fermented milk, yogurt, lactoprotein, casein, and whey protein and components thereof, brewed liquors such as refined sake, wine, Shaoxing, and beer, distilled liquors such as whiskey, brandy, and vodka.

To improve the survival ability in fermented milk foods or drinks using bacteria belonging to the genus *Bifidobacterium* during storage, containers made of oxygen-impermeable package materials such as glass and aluminum coated paper have been mainly used. As shown in the examples below, however, the microorganisms of the present invention have high oxygen tolerance and do not require a strictly anaerobic condition. Therefore, as container materials for the cholesterol absorption inhibitor of the present invention, highly oxygen-permeable resins (polystyrene, polyethylene, polyethylene terephthalate, etc.) can also be used. Containers using these resins are inexpensive and have advantages such as high degree of freedom in molding as compared with containers made of oxygen-impermeable package materials.

The microorganisms used as an active ingredient of the cholesterol absorption inhibitor of the present invention show excellent acid tolerance as shown in the examples below. Therefore, the cholesterol absorption inhibitor of the present invention can be made acidic. For example, its pH at 25° C. can be set to 2 to 7, in particular, 3 to 6.

The bacteria belonging to the genus *Bifidobacterium* used as an active ingredient of the cholesterol absorption inhibitor of the present invention have been utilized as food, and safety of these bacteria has been confirmed. Therefore, doses of these bacteria when used as a cholesterol absorption inhibitor are not strictly limited, but are preferably $10^5$ to $10^{13}$ cfu, particularly preferably $10^8$ to $10^{12}$ cfu per day as a viable cell count.

EXAMPLES

The present invention will be explained more specifically with reference to the following examples. However, the scope of the present invention is not limited to these examples.

Test Example 1

(1) Cholesterol Eliminating Activity

Bacterial cells were anaerobically cultured in m-ILS medium (Int. J. Food Microbiol. 81. 131-136, 2003) at 37° C. for 24 hours, the culture broth was centrifuged at 12,000 rpm and 4° C. for 15 minutes, and the bacterial cells were washed with 150 mM phosphate buffer (pH 5.5). The centrifugal washing was repeated three times, and the bacterial cells were suspended in 150 mM phosphate buffer to give turbidity (absorbance at 660 nm) of 3 (bacterial cell count of $10^8$-$10^9$ cfu/mL) to prepare a bacterial cell suspension. The bacterial cell suspension was further autoclaved at 121° C. for 15 minutes to prepare a dead bacterial cell suspension.

2 g of bovine bile powder, 921 mg of cholesterol, 135 mg of lysophosphatidylcholine, 90.2 mg of monooleic acid, and 702.2 mg of oleic acid were suspended in 150 mM phosphate buffer (pH 7.0), the suspension was ultrasonicated for 12 minutes and then ultracentrifuged at 100,000 G and 25° C. for 18 hours, and a micelle layer was collected to prepare artificial lipid micelles. 150 μL of artificial lipid micelles per mL of the bacterial cell suspension (bacterial cell count of $10^8$-$10^9$ cfu) was added, and the suspension was allowed to stand at 37° C. After 18 hours, the suspension was centrifuged at 12,000 rpm and 4° C. for 15 minutes, and cholesterols in the supernatant were quantified using Determiner TC555 (Kyowa Medics Co., Ltd.). A phosphate buffer containing no bacterial cell was similarly treated as a control, and the cholesterol eliminating activity was calculated by the following equation. Furthermore, the cholesterol eliminating activity was similarly calculated for the dead bacterial cell suspension.

Cholesterol eliminating activity(%)=100−(cholesterol level in supernatant containing bacterial cells)/ (cholesterol level in supernatant containing no bacterial cells)×100

(2) Acid Tolerance 0.1 ml of bacterial solution cultured in GAM medium (Nissui Pharmaceutical Co., Ltd.) to the stationary phase was added to 10 ml of 50 mM $Na_2HPO_4$ solution adjusted to pH 3 with hydrochloric acid, and the mixture was treated at 37° C. for 1 hour, and the survival rate was calculated by the following equation.

Survival rate(%)=(viable cell count after acid treatment)/(viable cell count before acid treatment)× 100

(3) Bile Acid Tolerance

30 μL of bacterial solution cultured in GAM medium to the stationary phase was inoculated in 3 mL of GAM medium containing 0.2% bile acid and anaerobically cultured at 37° C. After 24 hours, the bacterial cell turbidity was measured using Klett-Summerson Colorimeter (No. 66 Filter).

The test results of the above (1) to (3) are shown in Table 1.

TABLE 1

Results of determination of cholesterol eliminating activity, acid tolerance, and bile-acid tolerance of each bacterium

| | Cholesterol eliminating activity of viable bacterial cells (%) | Cholesterol eliminating activity of heated dead bacterial cells (%) | Acid tolerance (survival rate, %) | Bile-acid tolerance (klett value) |
|---|---|---|---|---|
| *Bifidobacterium animalis* subsp. *animalis* YIT 10394 | 85 | NT | 97 | 310 |
| *Bifidobacterium animalis* subsp. *lactis* JCM 1253 | 86 | NT | 117 | 256 |
| *Bifidobacterium animalis* subsp. *lactis* JCM 7117 | 79 | NT | 92 | 177 |

TABLE 1-continued

Results of determination of cholesterol eliminating activity,
acid tolerance, and bile-acid tolerance of each bacterium

| | Cholesterol eliminating activity of viable bacterial cells (%) | Cholesterol eliminating activity of heated dead bacterial cells (%) | Acid tolerance (survival rate, %) | Bile-acid tolerance (klett value) |
|---|---|---|---|---|
| Bifidobacterium pseudolongum subsp. globosum YIT 10392 | 77 | 2 | 100 | 153 |
| Bifidobacterium pseudolongum subsp. globosum YIT 10393 | 86 | 4 | 100 | 112 |
| Bifidobacterium adolescentis ATCC 15703 (type strain) | 20 | 6 | <1 | 198 |
| Bifidobacterium animalis subsp. animalis JCM 1190 (type strain) | 66 | 4 | 100 | 152 |
| Bifidobacterium angulatum ATCC 27535 (type strain) | 8 | NT | 12 | 108 |
| Bifidobacterium infantis ATCC 15697 (type strain) | 39 | NT | <1 | — |
| Bifidobacterium catenulatum ATCC 27539 (type strain) | 10 | 6 | <1 | 80 |
| Bifidobacterium pseudocatenulatum JCM 1200 (type strain) | 19 | 11 | <1 | 126 |
| Bifidobacterium bifidum IFO 14252 (type strain) | 13 | NT | <1 | — |
| Bifidobacterium breve ATCC 15700 (type strain) | 27 | 9 | <1 | 116 |
| Bifidobacterium longum ATCC 15707 (type strain) | 34 | 12 | <1 | — |

NT: not tested
<1: The survival rate was 1% or lower in examination of acid tolerance.
—: It was determined by visual examination that virtually no bacteria had grown in the bile-acid-added GAM medium in examination of bile-acid tolerance.

As shown in Table 1, *Bifidobacterium animalis* subsp. *animalis*, *Bifidobacterium animalis* subsp. *lactis* and *Bifidobacterium pseudolongum* subsp. *globosum* of the present invention showed a high cholesterol eliminating activity and were excellent in acid tolerance and bile-acid tolerance. Furthermore, since dead bacterial cells did not have a cholesterol eliminating activity, it was found that these bacteria show the activity in a viable cell state.

Subsequently, to find out whether elimination of cholesterols from the supernatant resulted from precipitation, or conversion or degradation, the cholesterol level in the precipitate portion was measured. As a result, it was found that cholesterols eliminated from the supernatant were not converted or degraded and existed in the precipitate. This result suggested the possibility that cholesterols in the supernatant might have been taken up into bacterial cells and precipitated, or lipid micelles might have been disintegrated by the bile acid deconjugating effect of bacterial cells or the like and precipitated.

Test Example 2

Effects on Blood Lipid and Hepatic Lipids in Animals

A 10% powdered skim milk medium containing 0.03% yeast extract were sterilized at 121° C. for 15 minutes, and *Bifidobacterium pseudolongum* subsp. *globosum* YIT 10393 was inoculated at 1% and anaerobically cultured for 24 hours. This culture broth was inoculated at 2% in the same medium and anaerobically cultured at 37° C. for 46 to 54 hours. The count of viable cells contained in the fermented milk thus prepared was $3.7 \times 10^8$ cfu/ml. This fermented milk was lyophilized, and a feed was prepared with a composition shown in Table 2. Here, the viable cell count in the feed was $1.0 \times 10^6$ cfu/g. Meanwhile, as a control, a 10% powdered skim milk medium containing 0.03% yeast extract was sterilized at 121° C. for 15 minutes and then lyophilized without inoculating bacteria as unfermented milk, and a feed was prepared with a composition shown in Table 2.

TABLE 2

| Composition of feed given to animals(%) | | |
|---|---|---|
| oligosaccharide | not added | added |
| casein | 19.66 | 19.66 |
| corn oil | 5 | 5 |
| vitamin mixture(AIN-93G) | 1 | 1 |
| mineral mixture(AIN-93G) | 3.5 | 3.5 |
| choline bitartrate | 0.2 | 0.2 |
| sucrose | 14.34 | 11.84 |
| α-corn starch | 50 | 50 |
| cellulose | 5 | 5 |
| DL-methionine | 0.3 | 0.3 |
| fermented milk or unfermented milk | 1 | 1 |
| galactooligosaccharide | 0 | 2.5 |

Subsequently, after 1 week of preliminary breeding, 8-week-old Wistar ovariectomized rats (purchased from Japan SLC) or sham rats were habituated to AIN-93G purified diet for 1 week and divided into the experimental groups shown in Table 3 depending on the body weight.

TABLE 3

| Experimental groups | | | |
|---|---|---|---|
| animals | milk | galactooligosaccharide % | no. of animals |
| sham | SM | 0 | 4 |
| OVX | SM | 0 | 5 |
| OVX | FSM | 0 | 5 |
| OVX | SM | 2.5 | 5 |
| OVX | FSM | 2.5 | 5 |

Sham: animals that underwent sham operation, OVX: animals that underwent ovariectomy, SM: unfermented milk, FSM: fermented milk The rats thus grouped were bred in individual bracket cages using the test feeds at room temperature of 24±1° C. and humidity of 55±5% with the feed corresponding to each group and water available ad libitum for 34 days. The daily intake of viable cells was about $10^7$ cfu/animal.

The animals were anesthetized with Nembutal. Food was withheld for 4 h before death. Blood was collected from the aorta ventralis, and the liver was collected under reflux. The liver was stored at −20° C. before analysis, and blood was centrifuged at 3000 rpm for 15 minutes to separate plasma. After lyophilization, the liver was extracted by the method of Folch (J. Biol. Chem. 226, 497-509, 1957).

The levels of total cholesterol and triglyceride contained in the plasma and liver extract thus obtained were obtained using Determiner TC555 (Kyowa Medics Co., Ltd.) and Triglyceride E-test Wako (Wako Pure Chemical Industries, Ltd.), respectively. Further, the level of HDL cholesterol contained in plasma was obtained using HDL-cholesterol E-test Wako (Wako Pure Chemical Industries, Ltd.). Further, the level of VLDL+LDL cholesterol contained in plasma was obtained by deducting the HDL cholesterol level from the total cholesterol level.

Based on the obtained results, p value was obtained for the ovariectomy group by two-way analysis of variance. Further, t test was performed between the ovariectomized rats and the sham rats, both of which given same feed. The obtained results are shown in Tables 4 to 6. The values were expressed with mean±SD. In Tables 4 to 6, the term "interaction" means an interaction between fermented milk and galactooligosaccharide.

TABLE 4

Effect of fermented milk prepared using *bifidobacterium pseudolongum* subsp. *globosum* YIT 10393 on growth

| | sham group unfermented milk | ovariectomy group | | | | result of analysis of variance (p<) | | |
| | | unfermented milk | | fermented milk | | | | |
| | without oligosaccharide | without oligosaccharide | with oligosaccharide | without oligosaccharide | with oligosaccharide | fermented milk | oligosaccharide | interaction |
|---|---|---|---|---|---|---|---|---|
| initial body weight (g) | 157 ± 6 | 182 ± 7*** | 182 ± 6 | 183 ± 6 | 182 ± 8 | NS | NS | NS |
| final body weight (g) | 185 ± 6 | 235 ± 13*** | 233 ± 8 | 234 ± 14 | 232 ± 5 | NS | NS | NS |
| increase in body weight (g) | 28 ± 2 | 53 ± 6*** | 52 ± 6 | 52 ± 10 | 50 ± 7 | NS | NS | NS |
| amount of food ingested (g/34 days) | 372 ± 19 | 454 ± 37** | 433 ± 24 | 452 ± 35 | 425 ± 11 | NS | NS | NS |

,*A significant difference was observed between the sham/unfermented milk/without oligosaccharide group and the ovariectomy/unfermented milk/without oligosaccharide group on a level of significance of 0.01 or 0.001.
NS: No significance As shown in Table 4, ovariectomized rats had more body weight and ingested more food as compared with the sham group, as previously reported (J. Comp. Physiol. Physicol 88: 183-193, 1975). However, effects of the presence or absence of oligosaccharide or administration of fermented milk were not observed in the ovariectomy group, and the animals grew favorably.

TABLE 5

Effect of fermented milk prepared using *bifidobacterium pseudolongum* subsp. *globosum* YIT 10393 on lipids in blood

| | sham group unfermented milk | ovariectomy group | | | | result of analysis of variance (p<) | | |
| | | unfermented milk | | fermented milk | | | | |
| | without oligosaccharide | without oligosaccharide | with oligosaccharide | without oligosaccharide | with oligosaccharide | fermented milk | oligosaccharide | interaction |
|---|---|---|---|---|---|---|---|---|
| TC | 101.7 ± 3.7 | 134.7 ± 8.6* | 145.7 ± 25.5 | 124.5 ± 17.7 | 120.3 ± 10.3 | 0.05 | NS | NS |
| TG | 54.9 ± 11.9 | 77.1 ± 15.0 | 74.4 ± 35.3 | 58.5 ± 17.6 | 50.5 ± 9.4 | 0.05 | NS | NS |
| HDL-C | 67.5 ± 5.3 | 90.0 ± 15.0* | 91.3 ± 16.7 | 101.3 ± 16.8 | 100.3 ± 7.1 | NS | NS | NS |
| VLDL + LDL-C | 34.0 ± 4.2 | 44.7 ± 11.2 | 54.4 ± 9.6 | 23.2 ± 13.8 | 20.1 ± 11.9 | 0.0001 | NS | NS |
| AI | 0.507 ± 0.096 | 0.521 ± 0.197 | 0.598 ± 0.061 | 0.241 ± 0.178 | 0.204 ± 0.124 | 0.001 | NS | NS |

*A significant difference was observed between the sham/unfermented milk/without oligosaccharide group and the ovariectomy/unfermented milk/without oligosaccharide group on a level of significance of 0.05.
TC, total cholesterol (mg/dL); TG, triglyceride (mg/dL); HDL-C, HDL cholesterol (mg/dL); VLDL + LDL-C, VLDL + LDL cholesterol (mg/dL); AI, arteriosclerosis index (VLDL + LDL-C/HDL-C)
NS: No significance Furthermore, as shown in Table 5, effects of fermented milk prepared using *Bifidobacterium pseudolongum* subsp. *globosum* YIT 10393 were observed in cholesterols, triglyceride, VLDL+LDL cholesterol in blood and the arteriosclerosis index, and all these parameters decreased. In particular, the VLDL+LDL cholesterol level markedly decreased. Furthermore, although effects of oligosaccharide on these parameters and an interaction between fermented milk and oligosaccharide were not statistically significant, the levels of total cholesterol, triglyceride, and VLDL+LDL cholesterol in blood, and the arteriosclerosis index were the lowest in the animals treated with oligosaccharide and fermented milk. It is known that galactooligosaccharide is utilized specifically by bacteria belonging to the genus *Bifidobacterium*. Therefore, it was demonstrated that *Bifidobacterium pseudolongum* subsp. *globosum* YIT 10393 grows in the intestinal tract and decreases blood lipid levels effectively by administering fermented milk containing galactooligosaccharide. Furthermore, it is known that total blood cholesterol is elevated after ovariectomy, and an animal that underwent ovariectomy is useful as a postmenopausal hyperlipemia model. Comparison of data of the ovariectomy/unfermented milk/without oligosaccharide group and the sham group showed that ovariectomy in this test had been successful.

TABLE 6

Effect of fermented milk prepared using *bifidobacterium pseudolongum* subsp. *globosum* YIT 10393 on hepatic lipids

| | sham group unfermented milk | Ovariectomy group | | | | result of analysis of variance (p<) | | |
| --- | --- | --- | --- | --- | --- | --- | --- | --- |
| | | unfermented milk | | fermented milk | | | | |
| | without oligosaccharide | without oligosaccharide | with oligosaccharide | without oligosaccharide | with oligosaccharide | fermented milk | oligosaccharide | interaction |
| liver weight (g) | 6.5 ± 0.6 | 7.9 ± 0.8* | 7.5 ± 0.7 | 7.6 ± 1.0 | 7.3 ± 0.5 | NS | NS | NS |
| total cholesterol (mg/g) | 7.4 ± 0.8 | 7.1 ± 0.3 | 7.0 ± 0.4 | 7.3 ± 0.4 | 7.3 ± 0.4 | NS | NS | NS |
| total cholesterol (mg/liver) | 13.6 ± 1.6 | 16.6 ± 1.4* | 16.0 ± 1.3 | 16.0 ± 2.6 | 15.4 ± 0.43 | NS | NS | NS |
| triglyceride (mg/g) | 72.1 ± 12.7 | 137.7 ± 26.5** | 138.4 ± 28.8 | 117.7 ± 29.0 | 103.3 ± 11.1 | 0.05 | NS | NS |
| triglyceride (mg/liver) | 132.4 ± 23.8 | 325.8 ± 80.3** | 319.1 ± 97.7 | 268.4 ± 113.9 | 220.4 ± 29.6 | NS | NS | NS |

*,**A significant difference was observed between the sham/unfermented milk/without oligosaccharide group and the ovariectomy/unfermented milk/without oligosaccharide group on a level of significance of 0.05 or 0.01.
NS: No significance As shown in Table 6, the cholesterol content in the liver was not affected by the presence of oligosaccharide or administration of fermented milk, and lipids were not accumulated in the liver. A statistical significance was not observed in the triglyceride level per liver after administration of fermented milk, but the triglyceride content per g of the liver decreased.

Since the fermented milk prepared using *Bifidobacterium pseudolongum* subsp. *globosum* YIT 10393 decreased the total cholesterol, triglyceride, and VLDL+LDL cholesterol levels in blood and the arteriosclerosis index as shown above, it was found that this bacterium has a lipid metabolism ameliorating ability for not only cholesterol but various blood lipids and an effect of decreasing a risk of developing arteriosclerosis.

Test Example 3

Examination of Survival Ability in Fermented Milk 0.03% yeast extract was added to 10% powdered skim milk solution, and the mixture was sterilized, each of the bacteria of the present invention (*Bifidobacterium animalis* subsp. *animalis* YIT 10394, *Bifidobacterium animalis* subsp. *lactis* JCM 1253, *Bifidobacterium animalis* subsp. *lactis* JCM 7117, and *Bifidobacterium pseudolongum* subsp. *globosum* YIT 10392, *Bifidobacterium pseudolongum* subsp. *globosum* YIT 10393) was inoculated at 2% and cultured at 37° C. to pH 5.1±1.0, produced five kinds of fermented milk. Furthermore, as a control, a fermented milk was produced in the same manner using *Bifidobacterium longum* ATCC 15707.

10 ml each of the prepared fermented milk was poured into a glass test tube for anaerobic storage and a polypropylene tube for non-anaerobic (aerobic) storage and stored at 10° C. for 12 weeks. For anaerobic storage, the test tube was stoppered tightly with a butyl rubber plug under a nitrogen gas flow. For non-anaerobic storage, the lid of the polypropylene tube was closed loosely. Table 7 shows pH and viable cell count after the completion of culture. Table 8 shows changes in the bacterial cell count in non-anaerobic storage. Table 9 shows changes in the bacterial cell count in anaerobic storage.

TABLE 7 pH and viable cell count of each bacterium at completion of culture

|  | pH | viable cell count (cfu/ml) | culture time (h) |
|---|---|---|---|
| *Bifidobacterium animalis* subsp. *animalis* YIT 10394 | 5.06 | $9.1 \times 10^8$ | 27 |
| *Bifidobacterium animalis* subsp. *lactis* JCM 1253 | 5.13 | $5.9 \times 10^8$ | 30 |
| *Bifidobacterium animalis* subsp. *lactis* JCM 7117 | 5.19 | $1.4 \times 10^9$ | 30 |
| *Bifidobacterium pseudolongum* subsp. *globosum* YIT 10392 | 5.19 | $3.4 \times 10^8$ | 30 |
| *Bifidobacterium pseudolongum* subsp. *globosum* YIT 10393 | 5.14 | $6.2 \times 10^8$ | 30 |
| *Bifidobacterium longum* ATCC 15707 | 5.01 | $3.3 \times 10^8$ | 27 |

TABLE 8

Changes in viable cell count of each bacterium in fermented milk in storage at 10° C. under non-anaerobic (aerobic) condition

|  | at completion of culture | after 3 weeks | after 8 weeks | after 12 weeks |
|---|---|---|---|---|
| *Bifidobacterium animalis* subsp. *animalis* YIT 10394 | $9.1 \times 10^8$ | $5.0 \times 10^8$ | $4.5 \times 10^7$ | $4.1 \times 10^6$ |
| *Bifidobacterium animalis* subsp. *lactis* JCM 1253 | $5.9 \times 10^8$ | $4.2 \times 10^8$ | $3.9 \times 10^8$ | $3.7 \times 10^8$ |
| *Bifidobacterium animalis* subsp. *lactis* JCM 7117 | $1.4 \times 10^9$ | $1.3 \times 10^9$ | $1.0 \times 10^9$ | $7.0 \times 10^8$ |
| *Bifidobacterium pseudolongum* subsp. *globosum* YIT 10392 | $3.4 \times 10^8$ | $2.6 \times 10^8$ | $7.6 \times 10^7$ | $1.7 \times 10^7$ |
| *Bifidobacterium pseudolongum* subsp. *globosum* YIT 10393 | $6.2 \times 10^8$ | $3.9 \times 10^8$ | $3.9 \times 10^7$ | $3.0 \times 10^6$ |
| *Bifidobacterium longum* ATCC 15707 | $3.3 \times 10^8$ | $9.2 \times 10^3$ | — | — |

—: not detected

TABLE 9

Changes in viable cell count of each bacterium in fermented milk in storage at 10° C. under anaerobic condition

|  | at completion of culture | after 3 weeks | after 12 weeks |
|---|---|---|---|
| *Bifidobacterium animalis* subsp. *animalis* YIT 10394 | $9.1 \times 10^8$ | $1.0 \times 10^9$ | $4.7 \times 10^8$ |
| *Bifidobacterium animalis* subsp. *lactis* JCM 1253 | $5.9 \times 10^8$ | $5.9 \times 10^8$ | $1.0 \times 10^9$ |
| *Bifidobacterium animalis* subsp. *lactis* JCM 7117 | $1.4 \times 10^9$ | $1.4 \times 10^9$ | $1.4 \times 10^9$ |
| *Bifidobacterium pseudolongum* subsp. *globosum* YIT 10392 | $3.4 \times 10^8$ | $3.3 \times 10^8$ | $1.8 \times 10^8$ |
| *Bifidobacterium pseudolongum* subsp. *globosum* YIT 10393 | $6.2 \times 10^8$ | $4.1 \times 10^8$ | $1.0 \times 10^8$ |
| *Bifidobacterium longum* ATCC 15707 | $3.3 \times 10^8$ | $4.5 \times 10^7$ | $4.2 \times 10^6$ |

As shown in Table 8, after 3 weeks of storage under non-anaerobic (aerobic) condition, *Bifidobacterium longum* ATCC 15707 used as a control was decreased to $9.2 \times 10^3$ cfu/mL and was not detected after 8 weeks. On the other hand, no bacterial strain of the present invention was decreased to below $1 \times 10^8$ cfu/mL even after 3 weeks of storage, and the survival rate was 50% or higher as compared with the cell count at completion of the culture. Furthermore, after 12 weeks of storage, *Bifidobacterium animalis* subsp. *lactis* JCM 1253 and *Bifidobacterium animalis* subsp. *lactis* JCM 7117 were not below $1 \times 10^8$ cfu/mL, and the remaining three bacterial strains (*Bifidobacterium pseudolongum* subsp. *globosum* YIT 10392, *Bifidobacterium pseudolongum* subsp. *globosum* YIT 10393, and *Bifidobacterium animalis* subsp. *animalis* YIT 10394) were decreased only by about 1 to 2 orders.

As shown in Table 9, after 3 weeks of storage under anaerobic condition, the bacterial cell count of *Bifidobacterium longum* ATCC 15707 decreased to about 1/10. However, the bacterial cell counts of the *Bifidobacterium* bacteria of the present invention at the completion of culture were virtually maintained. The bacterial cell counts of *Bifidobacterium pseudolongum* subsp. *globosum* YIT 10392, *Bifidobacterium pseudolongum* subsp. *globosum* YIT 10393, and *Bifidobacterium animalis* subsp. *animalis* YIT 10394 decreased only to about ½ to ⅙ after storage for 12 weeks, and the bacterial cell counts of *Bifidobacterium animalis* subsp. *lactis* JCM 1253 and *Bifidobacterium animalis* subsp. *lactis* JCM 7117 remained virtually unchanged even after 12 weeks.

Prescription Example 1

Production of Tablet

Various components were mixed, granulated, dried, and sized according to the following prescription and tableted to produce a tablet.

| (Prescription) | (mg) |
|---|---|
| Dried bacterial cells of the bacterium of the present invention[1] | 20 |
| Microcrystalline cellulose | 100 |
| Lactose | 80 |
| Magnesium stearate | 0.5 |
| Methylcellulose | 12 |

[1] Obtained by lyophilization of viable cells of *Bifidobacterium pseudolongum* subsp. *globosum* YIT 10392.

Prescription Example 2

Production of Fermented Milk Drink

3% glucose was added to 15% powdered skim milk solution, the mixture was sterilized, and *Bifidobacterium pseudolongum* subsp. *globosum* YIT 10393 was inoculated at 1% and anaerobically cultured at 35° C. for 24 hours to obtain 210 g of fermented milk base. Meanwhile, 97 g of sugar and 0.2 g of emulsified iron were dissolved in water to make 790 g as the total amount and sterilized to obtain a syrup. The fermented milk base and the syrup obtained as described above were mixed, followed by addition of 1 g of flavor, homogenized at 15 Mpa, and filled in a container to obtain a fermented milk drink. The obtained fermented milk drink was favorable in both appearance and taste, and the viable cell count immediately after production was $2.5 \times 10^8$ cfu/mL. Furthermore, storage stability was also favorable, with the viable cell count after storage at 10° C. for 21 days being $1.4 \times 10^8$ cfu/mL.

Prescription Example 3

Production of Soft Drink

Components of the following prescription were mixed and homogenized by a usual method to obtain a soft drink. The obtained soft drink was filled in a brown bottle, sealed with an aluminium cap, and subjected to heat treatment. The obtained soft drink was favorable in both appearance and taste, and storage stability was also favorable.

| (Prescription) | (g) |
|---|---|
| Dried bacterial cells of the bacterium of the present invention[1] | 5 |
| Flavor | 0.8 |
| Water | 100 |
| Glycosylated reduced starch | 24 |
| Fructose | 18 |

[1] Obtained by lyophilization of viable cells of *Bifidobacterium animalis* subsp. *animalis* YIT 10394.

The invention claimed is:

1. An isolated or purified bacterium or bacteria selected from the group consisting of *Bifidobacterium animalis* subsp. *animalis* YIT 10394 (FERM ABP-10662), *Bifidobacterium pseudolongum* subsp. *globosum* YIT 10392 (FERM ABP-10660), and *Bifidobacterium pseudolongum* subsp. *globosum* YIT 10393 (FERM ABP-10661).

2. The bacterium or bacteria of claim 1 which is *Bifidobacterium anirnalis* subsp. *animalis* YIT 10394 (FERM ABP-10662).

3. The bacterium or bacteria of claim 1 which is *Bifidobacterium pseudolongum* subsp. *globosum* YIT 10392 (FERM ABP-10660).

4. The bacterium or bacteria of claim 1 which is *Bifidobacterium pseudolongum* subsp. *globosum* YIT 10393 (FERM ABP-10661).

5. A composition comprising:
the isolated or purified bacterium or bacteria of claim 1, and
cholesterol.

6. The composition of claim 5 which is a food.

7. The composition of claim 5 which is an animal feed.

8. A method for reducing cholesterol in a subject comprising administering to said subject the isolated or purified bacterium or bacteria of claim 1 in an amount sufficient to reduce the level of cholesterol in the blood of said subject.

* * * * *